(12) United States Patent
Freeman et al.

(10) Patent No.: US 8,734,521 B2
(45) Date of Patent: May 27, 2014

(54) ASYMMETRIC DISC DISTRACTING CAGE

(75) Inventors: Thomas B Freeman, Tampa, FL (US); Wesley Johnson, Tampa, FL (US)

(73) Assignee: University of South Florida, Tampa, FL (US)

( * ) Notice: Subject to any disclaimer, the term of this patent is extended or adjusted under 35 U.S.C. 154(b) by 293 days.

(21) Appl. No.: 12/714,990

(22) Filed: Mar. 1, 2010

(65) Prior Publication Data

US 2010/0152857 A1    Jun. 17, 2010

Related U.S. Application Data

(63) Continuation-in-part of application No. PCT/US2008/075010, filed on Sep. 2, 2008.

(60) Provisional application No. 60/969,214, filed on Aug. 31, 2007.

(51) Int. Cl.
   *A61F 2/44* (2006.01)
(52) U.S. Cl.
   USPC .................................. 623/17.16; 623/17.11
(58) Field of Classification Search
   USPC ............................................ 623/17.16, 17.11
   See application file for complete search history.

(56) References Cited

U.S. PATENT DOCUMENTS

| | | |
|---|---|---|
| 6,443,987 B1 | 9/2002 | Bryan |
| 6,491,724 B1 | 12/2002 | Ferree |
| 6,558,424 B2 | 5/2003 | Thalgott |
| 6,660,038 B2 | 12/2003 | Boyer, II et al. |
| 6,743,255 B2 | 6/2004 | Ferree |
| 6,758,862 B2 | 7/2004 | Berry et al. |
| 6,796,983 B1 | 9/2004 | Zucherman et al. |
| 6,921,403 B2 | 7/2005 | Cragg et al. |
| 6,991,653 B2 | 1/2006 | White et al. |
| 7,014,659 B2 | 3/2006 | Boyer, II et al. |
| 7,029,498 B2 | 4/2006 | Boehm et al. |
| 7,077,864 B2 | 7/2006 | Byrd, III et al. |
| 7,087,082 B2 | 8/2006 | Paul et al. |
| 7,101,375 B2 | 9/2006 | Zucherman et al. |
| 2005/0143822 A1* | 6/2005 | Paul ........................ 623/17.16 |
| 2006/0241763 A1 | 10/2006 | Paul et al. |
| 2007/0118220 A1 | 5/2007 | Liu et al. |
| 2007/0191951 A1 | 8/2007 | Branch, Jr. |
| 2007/0233263 A1* | 10/2007 | Melkent et al. ............ 623/17.16 |
| 2008/0125865 A1* | 5/2008 | Abdelgany ................ 623/17.16 |

OTHER PUBLICATIONS

International Search Report for PCT/US08/77504 dated Nov. 24, 2008.
International Search Report for PCT/US08/075010 dated Nov. 10, 2008.

* cited by examiner

*Primary Examiner* — Andrew Yang
*Assistant Examiner* — Olivia C Chang
(74) *Attorney, Agent, or Firm* — David P. Hendricks; Michele L. Lawson; Smith & Hopen, P.A.

(57) ABSTRACT

An inter-vertebral cage with a wedge shape eccentrically located on the leading end of the cage. The ectopically shaped leading edge of this embodiment facilitates easier interbody spacer placement with less risk of nerve injury, as well as with likely decreased risk of destruction of the end plate during the distraction process when the interbody cage is impacted.

18 Claims, 8 Drawing Sheets

ASYMMETRIC DISC DISTRACTING CAGE

CROSS REFERENCE TO RELATED APPLICATIONS

This application is a continuation in part of prior filed International Application Serial Number PCT/US2008/075010 filed Sep. 2, 2008, which claims priority to U.S. Provisional Patent Application Ser. No. 60/969,214 filed Aug. 31, 2007; which are hereby fully incorporated by reference into this disclosure.

BACKGROUND OF THE INVENTION

This invention relates generally to spinal surgery and, in particular, to spinal cages of the type used in fusing adjacent vertebrae.

Surgeons frequently insert interbody cages in the thoracic and lumbar spine from a variety of approaches including posterior, lateral, oblique, transverse and anterior. Frequently, the disc space is degenerated and collapsed in these situations. Surgeons will often use the cage to distract the disc space as the cage is impacted into the disc space. One design utilizes a "bulleted" cage, such as the Capstone™ cage by Medtronic™. This design has a rounded wedge symmetrically disposed on the leading edge of the cage. This allows the anterior aspect of the cage to distract the disc space as it is impacted.

The problem is that such a cage has the distracting wedge shape directly in the medial aspect of the cage. With conditions such as listhesis in the setting of a collapsed disc, however, manipulation of the vertebrae from the medial aspect of the disc space is disadvantageous.

What is needed, therefore, is a mechanism which allows easier insertion of an inter-vertebral cage which also decreases the rate of end plate fracture with distraction and lessens the risk of nerve root injury with cage manipulation during the insertion process.

SUMMARY OF INVENTION

The invention, in a first embodiment, includes an inter-vertebral cage with a wedge shape eccentrically located on the leading end of the cage. The invention of this embodiment improves on wedge-shaped interbody spacers where the apex of the leading edge is in the center of the cage. The ectopically shaped leading edge of this embodiment facilitates easier interbody spacer placement with less risk of nerve injury, as well as with likely decreased risk of destruction of the end plate during the distraction process when the interbody cage is impacted.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention includes, in a general embodiment, a self-distracting inter-vertebral cage adapted to facilitate fusion between adjacent upper and lower spinal vertebrae. The device of a preferred embodiment, therefore, restores an optimal inter-vertebral space height and a normal lordosis. In use, the inventive device is driven into an inter-vertebral space to distract the vertebrae, as is discussed in greater detail below.

Many of the advantages provided by the inventive cage derive from its shape. For example, the unique anterior portion of the invention enables a practitioner to insert the cage into a collapsed-disc space, using the leading edge to selectively distract the adjacent vertebrae. Another advantage is the generally rectangular shape of the posterior portion of the invention, which enables the device to fit conveniently between adjacent vertebrae and further enhance fusion and distraction between the upper and lower vertebrae. The tight fit of the posterior portion in the inter-vertebral space also maintains the distraction of the disc space during fusion.

Figure 1:
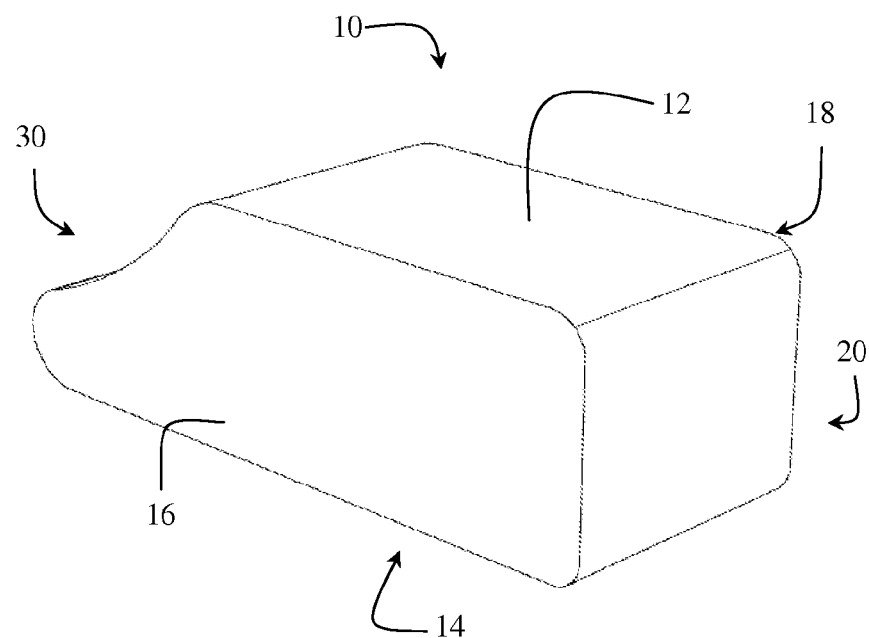
FIG. 1 is a perspective view of a general embodiment of the inventive interbody cage.

FIG. 1 illustrates a general embodiment of the invention. Asymmetric disc-distracting device 10 is presented in the form of a generally rectangular cage having superior and inferior surfaces 12 and 14, and first side 16 and second side 18, respectively.

Figure 2:
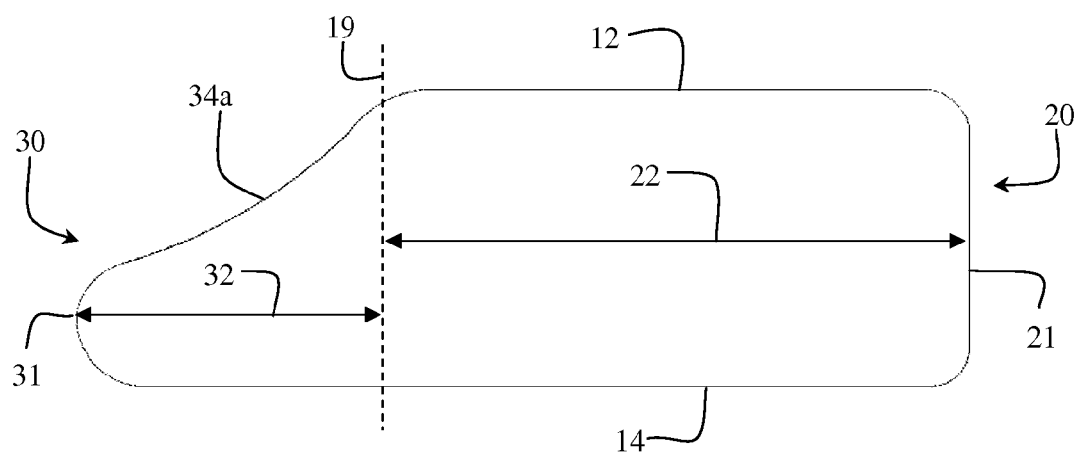
FIG. 2 is a side plan view of a first embodiment of the invention wherein the longitudinal axis of the anterior portion of the cage is inferior to the longitudinal axis of the posterior portion and the inferior surface of the anterior portion is coplanar with the inferior surface of the posterior portion.

Device 10, as shown in FIG. 2, also comprises substantially rectangular posterior portion 20 (facing generally to the right of the page), and generally tapering (or wedge-shaped) anterior portion 30 (facing generally leftward on the page). Anterior portion 30, in a preferred embodiment, extends integrally from posterior portion 20. Transverse plane 19 defines an artificial boundary between posterior portion 20 and anterior portion 30. Posterior portion 20 has a first longitudinal axis 22 and anterior portion 30 has a second longitudinal axis 32 relative to transverse plane 19. First longitudinal axis 22 is an imaginary line running across the approximate center of trailing wall 21 of posterior portion 20 perpendicular to transverse plane 19. Second longitudinal axis 32 extends from leading edge 31 of anterior portion 30 to transverse plane 19 and is parallel to first longitudinal axis 22. It can furthermore be seen in FIG. 2 that first longitudinal axis 22 and second longitudinal axis 32 are dis-planar with respect to transverse plane 19. This dis-planar relationship causes device 10 to be asymmetrical along its combined longitudinal axis.

The particular configuration of device 10, including anterior portion 30, in FIGS. 1 and 2 is provided for representative purposes and other asymmetrical shapes are contemplated. For example, device 10 is shown in FIGS. 1 and 2 as having parallel superior and inferior surfaces 12 and 14. Device 10 could, however, be made with superior surface 12 and inferior surfaces 14 at a predetermined angle thereby enhancing lordosis.

Figure 3A:
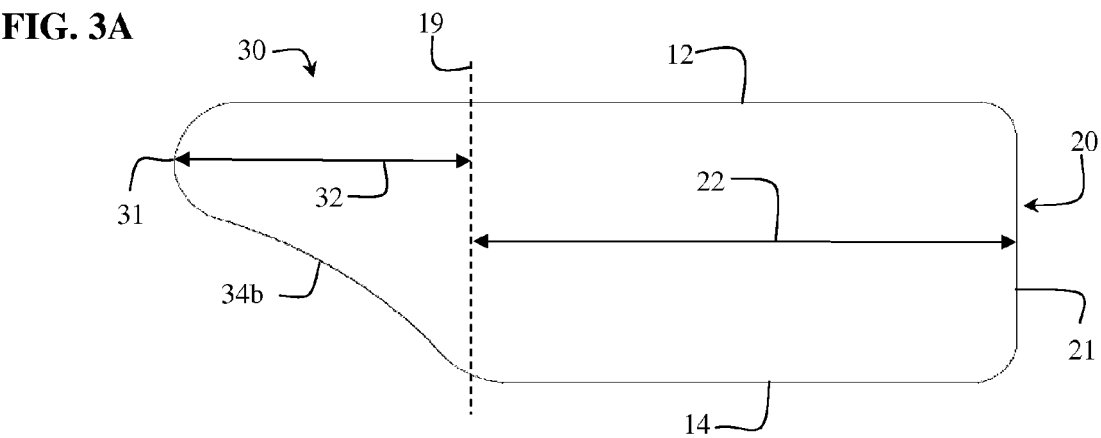
FIG. 3A is a side plan view of a second embodiment of the invention wherein the longitudinal axis of the anterior portion of the cage is superior to the longitudinal axis of the posterior portion and the superior surface of the anterior portion is coplanar with the superior surface of the posterior portion.
Figure 3B:
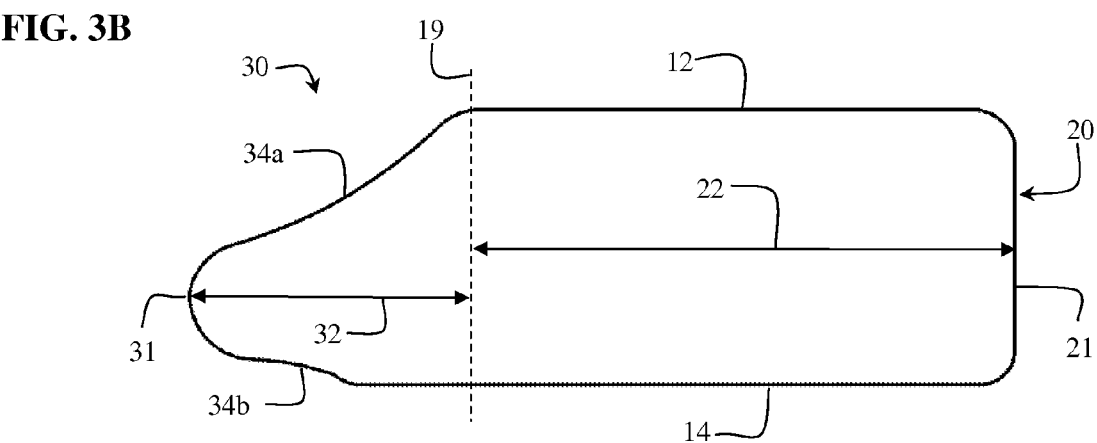
FIG. 3B is a side plan view of a third embodiment of the invention wherein the longitudinal axis of the anterior portion of the cage is inferior to the longitudinal axis of the posterior portion and the inferior surface of the anterior portion is superior to the inferior surface of the posterior portion.
Figure 3C:
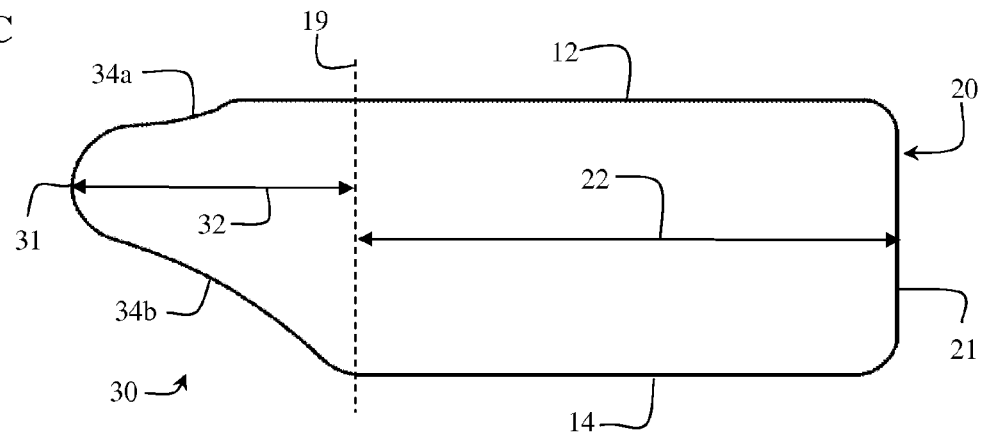
FIG. 3C is a side plan view of a fourth embodiment of the invention wherein the longitudinal axis of the anterior portion of the cage is superior to the longitudinal axis of the posterior portion and the superior surface of the anterior portion is inferior to the inferior surface of the posterior portion.

It is also contemplated that leading edge 31 can be disposed at any height which results in device 10 being asymmetrical along its combined longitudinal axis. Examples of alternate embodiments are shown in FIGS. 3A through 3C. Anterior portion 30, as shown, is substantially shorter than posterior portion 20. However; in another embodiment, anterior portion 30 is the same length or longer than posterior portion 20. A variety of other shapes and configurations are also contemplated.

The following represents illustrative dimensions for use in construction of the inventive device. The following dimensions are provided by way of example only and the skilled artisan will appreciate such. Accordingly, it is contemplated that the following dimensions can be altered to fit the specific needs of the practitioner. In this illustrative embodiment, the leading edge 31 can be anywhere from three to six millimeters, and the height of the cage can range in sizes in height from six to seventeen millimeters. The width of the cage can vary from six to eighteen millimeters for cages utilized from a posterior approach. If cages are inserted using an anterior approach, up to 45 mm wide cages might be used. Such larger cages could also utilize internal cross beams to help distribute load and increase cage strength. Such heights are standard for similar cages used in the industry. The length of the cage can vary anywhere from 18-40 millimeters, similar to other cage lengths standard in the art.

Referring again to FIGS. 2 through 3C, anterior portion 30 may be disposed with variations of superior slope 34a and/or inferior slope 34b. Accordingly, slopes 34a, 34b may be concave, parabolic, hyperbolic, elliptical, circular or any other shape as known in the art. Slopes 34a, 34b can also be linear or convex (hyperbolic, elliptical, circular or any other shape as known in the art). Additionally, superior surface 12 and/or inferior surface 14 may also be concave and/or convex, as needed, to better engage adjacent vertebral endplates. In still another embodiment, the trailing end of posterior portion 20 may be wider, relative to the lateral thickness of anterior portion 30, to provide additional strength in compression of the posterior spine.

Various materials may be used in the construction of device 10. Illustrative materials include, but are not limited to, stainless steel, cobalt-chromium-molybdenum alloys, titanium, carbon reinforced polymers, shape memory alloys, materials commonly used for commercial and industrial springs, and nylon or other fiber or polymer materials used for the radiolucent screen or mesh sleeve. Further examples of carbon reinforced polymers include polyether ether ketone, (polyether ketone, ether ketone, and ketone), polycarbonate, polypropylenes, polyethylene and polysulfone type plastic materials with or without glass or carbon fibers.

Figure 4A:
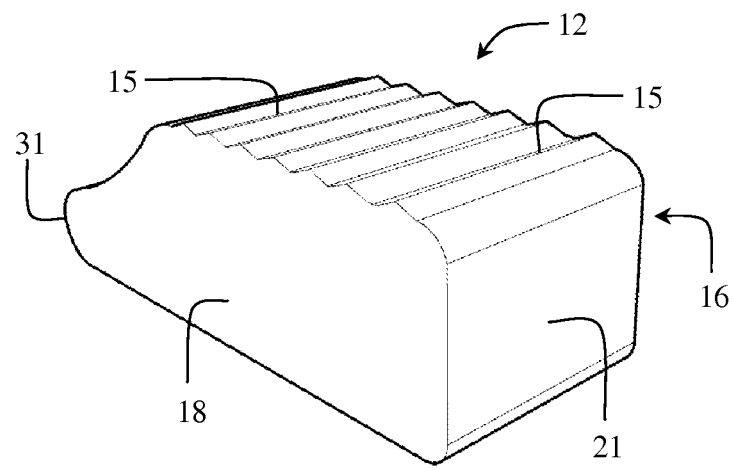
FIG. 4A is a rear perspective view of a fifth embodiment of the invention wherein the superior surface of the posterior portion contains serrations.
Figure 4B:
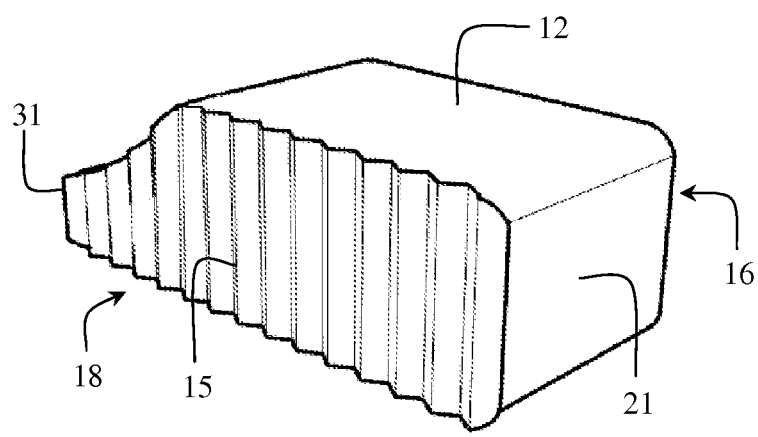
FIG. 4B is a rear perspective view of a sixth embodiment of the invention wherein the opposing sides of the device contain serrations.

In yet another embodiment, shown in FIG. 4A, superior surface 12 and/or inferior surface 14 may include serrations 15, or alternative surfacing to better engage the endplates of the adjacent vertebrae. In an alternate embodiment, shown in FIG. 4B, at least one of the opposing sides (16 and 18 respectively) has a plurality of serrations 15 thereon. Serrations 15 help device 10 remain in place once inserted between the vertebrae. Serrations 15 may be angled to allow ready insertion of device 10 in the distal, anterior direction and prevent retraction in the proximal, posterior direction. The implanted device therefore remains between adjacent vertebrae.

Figure 5A:
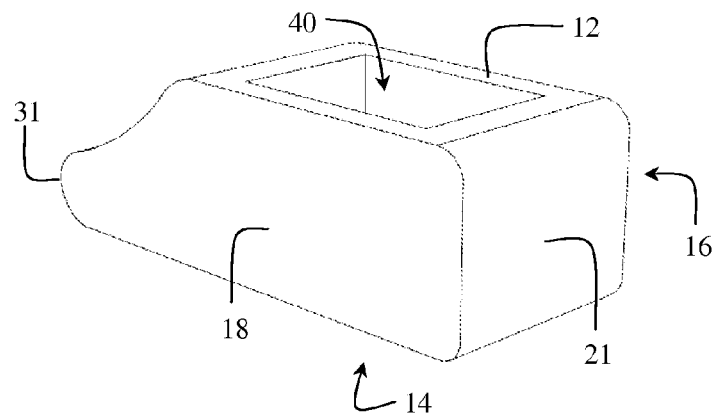
FIG. 5A is a perspective view of yet another embodiment wherein the superior surface of the posterior portion is apertured, thereby providing communication with the bone growth chamber.
Figure 5B:
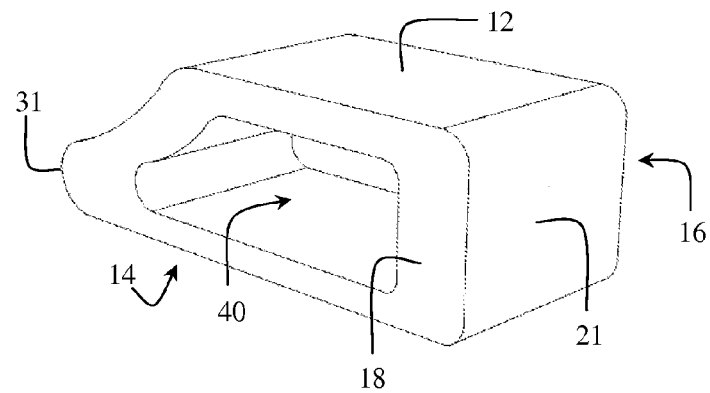
FIG. 5B is a perspective view of alternate embodiment of the cage of FIG. 5A wherein the opposing sides of the posterior portion are apertured, thereby providing communication with the bone growth chamber.

In another embodiment, shown in FIGS. 5A and 5B, at least one surface (i.e. superior surface 12, inferior surface 14, first side 16 or second side 18) are apertured to provide communication with interior chamber 40. Chamber 40 is provided for the inclusion of an osteogenic material. The osteogenic material is advantageous in that device 10 fosters bone growth and permits the upper and lower vertebrae (as well as to adjacent bone fragments placed within the inter-vertebral space) to fuse to device 10. The use of an osteogenic material in the fusion encourages bone growth and, as such, bone will grow from those adjacent bone sources having adequate blood supply. Over time, bone from the adjacent vertebrae grows into chamber 40, and completely incorporates device 10.

Any suitable osteogenic material or composition is contemplated for placement within the chamber 40. Illustrative osteogenic material include, for example, autograft, allograft, xenograft, demineralized bone, synthetic and natural bone graft substitutes, such as bio-ceramics and polymers, and osteo-inductive factors. Where bony material is placed within the chamber 40, the material can be pre-packed before the device is implanted, or can be inserted through the apertures after the device is in position. A separate carrier to hold the materials within the chambers of the device can also be used. These carriers can include collagen-based carriers, bio-ceramic materials, hydroxyapatite and calcium phosphate compositions. The carrier material can be provided in the form of a sponge, a block, folded sheet, putty, paste, graft material or other suitable form. Moreover, the osteogenic compositions contained within the vertebral replacement device can comprise an effective amount of a bone morphogenetic protein, transforming growth factor .beta.1, insulin-like growth factor 1, platelet-derived growth factor, fibroblast growth factor, LIM mineralization protein (LMP), and combinations thereof or other therapeutic or infection resistant agent, held within a suitable carrier material.

Figure 6A:
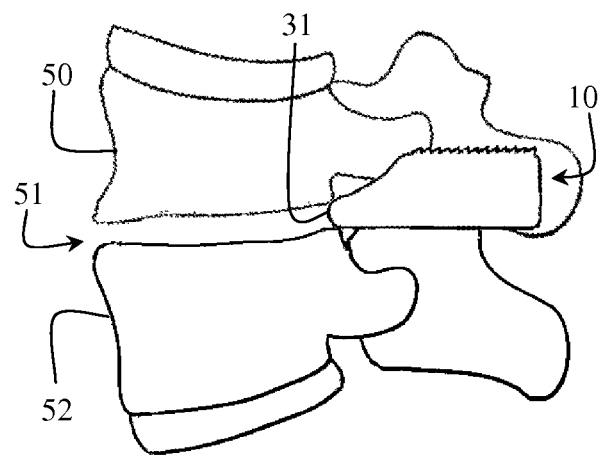
FIG. 6A is a diagrammatic view of the leading edge of the device prior to insertion in the disc space.
Figure 6B:
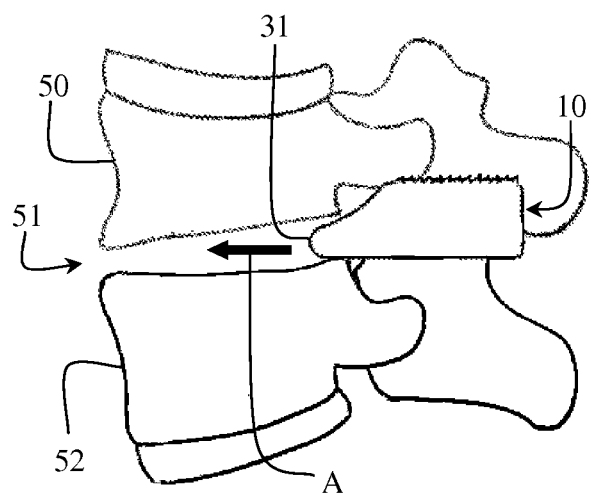
FIG. 6B is a diagrammatic view of the leading edge of the device during insertion in the disc space.
Figure 6C:
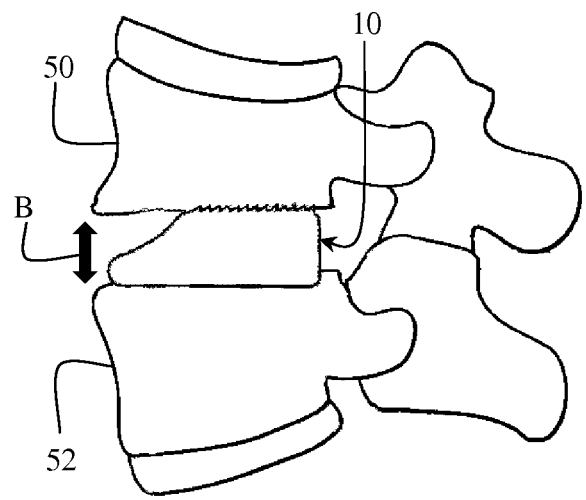
FIG. 6C is a diagrammatic view of the device after insertion in the disc space.
Figure 6D:
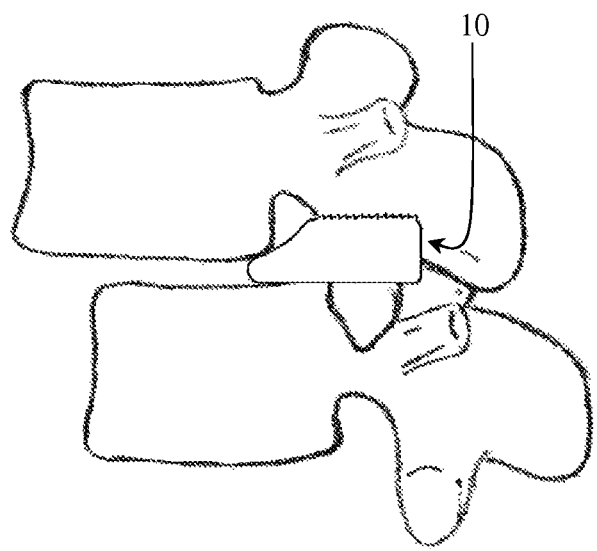
FIG. 6D is a diagrammatic view of the device for application in Spondylolisthesis condition.

With reference now to FIGS. 6A through 6C, an example of the placement of device 10 disc space 51 between upper vertebrae 50 and adjacent lower vertebrae 52 is shown. The example provided depicts the posterior lumbar interbody fusion (PLIF) method. Device 10, however, has equal functionality in the anterior lumbar interbody fusion (ALIF) method. As shown in FIG. 6A, leading edge 31 is positioned posteriorly between upper and lower vertebrae 50, 52 adjacent disc space 51. In FIG. 6B, device 10 is driven anteriorly (as indicated by arrow A) into disc space 51 between adjacent vertebrae 50, 52. FIG. 6C shows device 10 in substantially locked engagement between adjacent vertebrae 50, 52. Device 10 provides the desired level of distraction (as indicated by arrow B) of the anterior portions of adjacent vertebrae 50, 52.

Figure 7A:
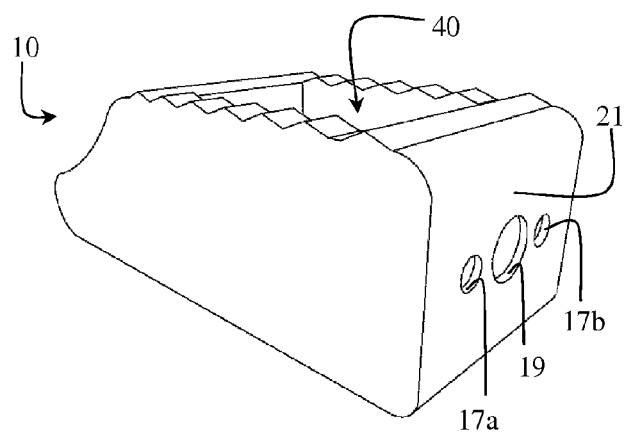
FIG. 7A is a rear perspective view of the device with associated insertion features such as screw holes.

With reference now to FIG. 7A, an alternate embodiment is shown wherein trailing wall 21 includes manipulation holes 17a and 17b, extending at least partially there through, which provide for temporarily coupling device 10 to an insertion device (not shown). Devices for inserting cages embody a variety of patents including threaded screws and paddles which hold the posterior edge. Impacters come in a variety of forms as well. Central hole 19 extends through the trailing wall 21 to chamber 40. Central hole 19 is used to manipulate device 10 as well as provide communication chamber 40 and the surrounding vertebral structures.

Figure 7B:
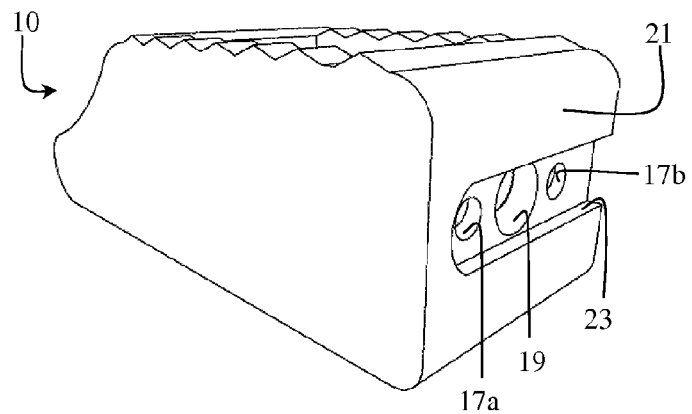
FIG. 7B is a rear perspective view of an alternate embodiment of the device of FIG. 7A wherein the associated insertion features are recessed.
Figure 7C:
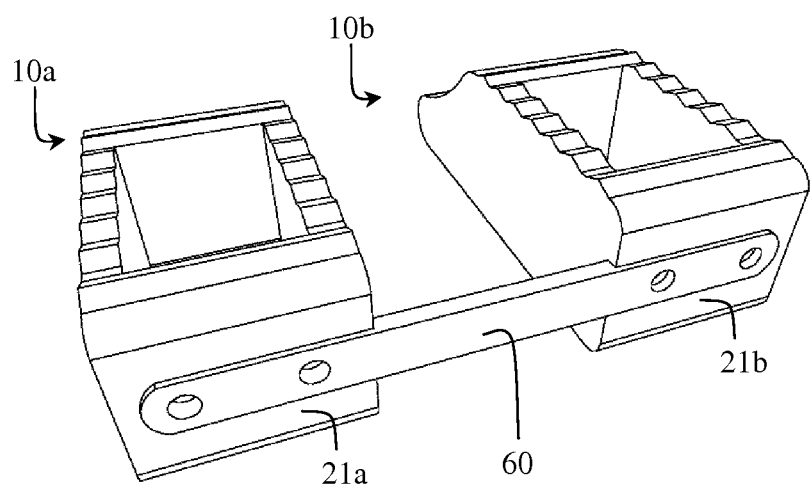
FIG. 7C is a rear perspective view of two connected devices.

In a particular embodiment, shown in FIG. 7B, screw holes 17a and 17b are formed in recess 23 which extends to one side of device 10 to accommodate a connecting bar, as shown in FIG. 7C. In FIG. 7C, first and second devices 10a, 10b are shown. In such an embodiment first and second devices are maintained between the upper and lower vertebrae such that the two devices simultaneously provide fusion potential and balance the vertebrae thereon. FIG. 7C illustrates one way two devices according to the invention may be interlocked using connector 60 with mechanical fasteners such as screws (not shown). Connector 60 fits into a recess 23 (FIG. 7B) provided on trailing walls 21a and 21b of the devices to prevent rotation. Note that devices 10a and 10b may be independent of one another in terms of the various embodiments discussed herein. Accordingly, they need not assume the same wedge size once implanted, but rather, may be different to accommodate spinal defects or other aspects of patient physiology.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. An asymmetric inter-vertebral cage, consisting of:
    a singular, asymmetric frame having anterior and posterior portions, superior and inferior surfaces, and two opposing sides;
    the thickness of the frame between the superior and inferior surfaces in the anterior portion defining an anterior height;
    the anterior portion having first longitudinal axis;
    the thickness of the frame between the superior and inferior surfaces in the posterior portion defining a posterior height;
    the posterior portion having a second longitudinal axis;
    the anterior portion comprising a leading edge extending in a convex arc from the inferior surface upwards toward the superior surface, the convex arc terminating at a transition point located at a distance less than half of the posterior height as measured from the inferior surface, and the leading edge continuing from the transition point in a concave arc to the superior surface;
    wherein the anterior height is less than the posterior height; and
    wherein the first longitudinal axis is dis-planar in relation to the second longitudinal axis thus making the device asymmetrical along its combined longitudinal axis.

2. The inter-vertebral cage of claim 1, wherein the first longitudinal axis is inferior to the second longitudinal axis.

3. The inter-vertebral cage of claim 1, wherein the first longitudinal axis is superior to the second longitudinal axis.

4. The inter-vertebral cage of claim 1, wherein the interior volume of the frame is substantially unoccupied to receive bone graft material.

5. The inter-vertebral cage of claim 4, wherein the superior surface has an aperture in communication with the interior volume of the frame.

6. The inter-vertebral cage of claim 4, wherein at least one of the opposing sides has an aperture in communication with the interior volume of the frame.

7. The inter-vertebral cage of claim 1, wherein the superior and inferior surfaces include protrusions for frictionally engaging with vertebral endplates defining the disk space.

8. The inter-vertebral cage of claim 1, wherein the two opposing sides include protrusions for frictionally engaging with vertebral endplates defining the disk space.

9. The inter-vertebral cage of claim 1, wherein the superior and inferior surfaces are substantially parallel.

10. An asymmetric inter-vertebral cage assembly, consisting of:
    a plurality of asymmetric frames with each frame having anterior and posterior portions, superior and inferior surfaces, and a first and a second opposing side;
    the thickness of each frame between the superior and inferior surfaces in the anterior portion defining an anterior height;
    the anterior portion having first longitudinal axis;
    the thickness of each frame between the superior and inferior surfaces in the posterior portion defining a posterior height;
    the posterior portion having a second longitudinal axis;
    the anterior portion comprising a leading edge extending in a convex arc from the inferior surface upwards toward the superior surface, the convex arc terminating at a transition point located at a distance less than half of the posterior height as measured from the inferior surface, and the leading edge continuing from the transition point in a concave arc to the superior surface;
    wherein the anterior height is less than the posterior height;
    wherein the first longitudinal axis is dis-planar in relation to the second longitudinal axis thus making the device asymmetrical along its combined longitudinal axis; and
    a connector associated with the posterior portion of each frame for interconnecting the plurality of asymmetric frames together at their respective posterior portions such that the first opposing side of a first frame is oriented to be parallel with the second opposing side of a second frame within the same inter-vertebral space.

11. The inter-vertebral cage assembly of claim 10, wherein the first longitudinal axis is inferior to the second longitudinal axis.

12. The inter-vertebral cage assembly of claim 10, wherein the first longitudinal axis is superior to the second longitudinal axis.

13. The inter-vertebral cage assembly of claim 10, wherein the interior volume of each frame is substantially unoccupied to receive bone graft material.

14. The inter-vertebral cage assembly of claim 13, wherein the superior surface has an aperture in communication with the interior volume of each frame.

15. The inter-vertebral cage assembly of claim 13, wherein at least one of the opposing sides has an aperture in communication with the interior volume of the frame.

16. The inter-vertebral cage assembly of claim 10, wherein the superior and inferior surfaces include protrusions for frictionally engaging with vertebral endplates defining the disk space.

17. The inter-vertebral cage assembly of claim 10, wherein the first and the second opposing sides include protrusions for frictionally engaging with vertebral endplates defining the disk space.

18. The inter-vertebral cage assembly of claim 10, wherein the superior and inferior surfaces are substantially parallel.

* * * * *